US005507973A

United States Patent [19]
Rieke

[11] Patent Number: 5,507,973
[45] Date of Patent: *Apr. 16, 1996

[54] HIGHLY REACTIVE ZEROVALENT METALS FROM METAL CYANIDES

[75] Inventor: Reuben D. Rieke, Lincoln, Nebr.

[73] Assignee: Board of Regents of the University of Nebraska, Lincoln, Nebr.

[ * ] Notice: The term of this patent shall not extend beyond the expiration date of Pat. No. 5,358,546.

[21] Appl. No.: 893,501

[22] Filed: Jun. 4, 1992

Related U.S. Application Data

[63] Continuation-in-part of Ser. No. 692,236, Apr. 26, 1991, abandoned.

[51] Int. Cl.$^6$ .................................................. C09K 3/00
[52] U.S. Cl. ........................................................ 252/182.12
[58] Field of Search ............................................. 252/182.12

[56] References Cited

U.S. PATENT DOCUMENTS

| | | | |
|---|---|---|---|
| 3,100,782 | 8/1963 | Joly et al. | |
| 3,660,443 | 5/1972 | Boissieras et al. | |
| 3,755,395 | 8/1973 | Bakassian et al. | |
| 3,948,803 | 4/1976 | Carney | 585/462 |
| 4,087,468 | 5/1978 | Solomon | |
| 4,152,303 | 5/1979 | Cohen et al. | 502/243 |
| 4,595,572 | 6/1986 | Ogasa et al. | |
| 4,705,881 | 11/1987 | Rapoport | 558/338 |
| 5,211,889 | 5/1993 | Rieke | 556/110 |
| 5,358,546 | 10/1994 | Rieke | 556/118 |

FOREIGN PATENT DOCUMENTS

| | | |
|---|---|---|
| 252766 | 1/1988 | European Pat. Off. |
| 61-019707A2 | 1/1986 | Japan |

OTHER PUBLICATIONS

E. Bouhlel et al., "A Convenient Procedure for the Preparation of Reactive Zinc for the Reformatsky Reaction", *Synthetic Communications*, 21, 133–136 (1991).

B. T. Dawson, "I. Chemistry of (Eta(5):Eta(5)–Biphenyl) (Chromium Tricarbonyl) (2) Dianions. II. Two Equivalent Reduction of Copper(I) Salts. III. A New Rieke Active Copper: Reduction of a Copper Cyanide Lithium Halide Complex (Copper Cyanide, Lithium Halide, Biphenylchromium Tricarbonyl)", Abstract of Ph.D. Thesis, The University of Nebraska–Lincoln (1992).

R. A. O'Brien, "Chemical Modification of Halogenated Polystyrene Resins Utilizing Highly Reactive Copper and Calcium and the Chemistry of Highly Reactive Copper Contained in a Polymer", Ph.D. Thesis, The University of Nebraska–Lincoln (1992).

S. J. Uhm, "Preparation of Activated Zinc Metal and Its Reactions with Organic Halides in Presence of Various Lewis Bases", Ph.D. Thesis, The University of Nebraska–Lincoln (1974).

R. M. Wehmeyer, "The Preparation and Chemistry of Active Copper, Nickel, and Zinc", Ph.D. Thesis, The University of Nebraska–Lincoln (1988).

H. Xiong, "Chemistry of Conjugated Diene–Magnesium Reagents: A Novel Approach to Cyclic and Functionalized Molecules", Ph.D. Thesis, The University of Nebraska–Lincoln (1992).

L.–S. Zhu, "The Preparation of Novel Organozinc Reagents Using Highly Reactive Zinc", Ph.D. Thesis, The University of Nebraska–Lincoln (1991).

Abstract of the National Institute of Health Grant No. GM35153 (1992).

K. J. Klabunde et al., *J. Org. Chem.*, 44, 3901–3908 (1979).

P. Knochel et al., *J. Org. Chem.*, 53, 2390–2392 (1988).

B. E. Lenk, M.S. Thesis, University of Nebraska, Lincoln, Nebraska, 1988.

T. O. Murdock et al., *J. Org. Chem.*, 41, 1076–1077 (1976).

E–I. Negishi, *Organometallics in Organic Synthesis*, New York: Wiley (1980).

M. S. Newman et al., *J. Amer. Chem. Soc.*, 77, 946–947 (1955).

R. A. O'Brien et al., *J. Org. Chem.*, 55, 788–790 (1990).

G. Picotin et al., *J. Org. Chem.*, 52, 4796–4798 (1987).

R. D. Rieke, *J. Chem. Soc., Chem. Commun.*, 269–270 (1973).

R. D. Rieke et al., *J. Am. Chem. Soc.*, 96, 1775–1781 (1974).

R. D. Rieke et al., *J. Organomet. Chem.*, 76, C19–C21 (1974).

R. D. Rieke et al., *Syn. React. Inorg. Metal–Org. Chem.*, 4, 101–105 (1974).

R. D. Rieke, *Use of Activated Metals in Organic and Organometallic Synthesis*, Springer–Verlag: New York (1975), pp. 1–31.

R. D. Rieke et al., *Synthesis*, 452–453 (1975).

R. D. Rieke, *Accounts of Chem. Res.*, 10, 301–306 (1977).

R. D. Rieke, *Gov. Rep. Announce. Index (U.S.)*, 78, 171 (1978) (U.S. NTIS, AD Rep., No. AD–A045863, 1977).

R. D. Rieke, *J. Org. Chem.*, 46, 4323–4324 (1981).

R. D. Rieke, *Gov. Rep. Announce. Index (U.S.)*, 85, 54 (1985) U.S. NTIS, AD Rep., No. AD–A150026/3/GAR. Abstract of preceding reference: R. D. Rieke, *Chem. Abs.*, 103, 31489r (1985).

R. D. Rieke et al., *High Energy Processes in Organometallic Chemistry*, ACS Symposium Series No. 333, ACS 1987, Ch. 14, 223–245.

R. D. Rieke et al., *Tetrahedron*, 45, 443 (1989).

R. D. Rieke, *Science*, 246, 1260–1264 (1989).

(List continued on next page.)

*Primary Examiner*—Edward A. Miller
*Attorney, Agent, or Firm*—Merchant, Gould, Smith, Edell, Welter & Schmidt

[57] ABSTRACT

Novel zerovalent metal species and organometallic reagents are disclosed. The zerovalent metal species are directly produced by reaction of a reducing agent on a metal cyanide salt. Preferably, the zerovalent metal species are directly produced by reaction of an alkali metal reducing agent with a metal cyanide salt. The organometallic reagent results from the reaction of the zerovalent metal species and an organic compound having one or more stable anionic leaving groups.

3 Claims, No Drawings

OTHER PUBLICATIONS

R. D. Rieke et al., *Synth. Commun.*, 19, 1833–1840 (1989).
R. D. Rieke et al., *Synth. Commun.*, 20, 2711–2721 (1990).
D. E. Stack et al., *J. Am. Chem. Soc.*, 113, 4672–4673 (1991).
K. Takeda et al., *Bull. Chem. Soc. Jpn.*, 41, 268 (1968).
R. M. Wehmeyer et al., *Tetrahedron Lett.*, 29, 4513–4516 (1988).
T–C. Wu et al., *Tetrahedron Lett.*, 29, 6753–6756 (1988).
T–C. Wu et al., *J. Org. Chem.*, 55, 5045–5051 (1990).
M. C. P. Yeh et al., *Tetrahedron Letters*, 29, 2395–2396 (1988).
M. C. P. Yeh et al., *Tetrahedron Letters*, 29, 6693–6696 (1988).
L. Zhu et al., *J. Org. Chem.*, 56, 1445–1453 (1991).
R. F. Abdulla, *Aldrichimica Acta*, 21, 31–42 (1988).
D. J. Burton et al., *J. Org. Chem.*, 54, 613–617 (1989).
L–C. Chao et al., *J. Org. Chem.*, 40, 2253–2255 (1975).
G. W. Ebert et al., *J. Org. Chem.* 49, 5280–5282 (1984).
G. W. Ebert et al., *J. Org. Chem.*, 53, 4482–4488 (1988).
E. Erdik, *Tetrahedron*, 43, 2203–2212 (1987).
B–H. Han et al., *J. Org. Chem.*, 47, 5030–5032 (1982).
B. H. Han et al., *J. of the Korean Chemical Society*, 29, 557–558 (1985).
S–I. Inaba et al., J. Org. Chem., 50, 1373–1381 (1985).
B. E. Kahn et al., Abstract for "Preparation of Active Uranium in Hydrocarbon Solvents and Its Reactions with Oxygen Containing Compounds" presented at American Chemical Society 192nd Meeting, Anaheim, CA, Sep. 7–12, 1986.
A. V. Kavaliunas et al., *Organometallics*, 2, 377–383 (1983).
R. A. Kjonaas et al., *J. Org. Chem.*, 51, 3993–3996 (1986).

HIGHLY REACTIVE ZEROVALENT METALS FROM METAL CYANIDES

The present invention was made with Government support under Contract No. GM35153 awarded by the National Institute of Health. The Government has certain rights in the invention.

CROSS REFERENCE TO RELATED APPLICATIONS

This application is a continuation in part of application Ser. No. 07/692,236, filed Apr. 26, 1991, now abandoned.

BACKGROUND OF THE INVENTION

Highly reactive zerovalent metals are desirable reagents for the synthesis of new organic and organometallic compounds. They can be used in the synthesis of many drugs, agrochemicals, monomers for use in polymers, highly conducting polymers, dyes, synthetics fibers, fluorocarbons, and a long list of other specialty chemicals. They can also be used in the preparation of novel information storage devices, nonlinear optical materials, and novel batteries. They are particularly useful in the reactions of organic and inorganic substrates, either in a catalytic fashion or with the consumption of the metal.

There have been numerous approaches used to increase the reactivity of zerovalent metals. This is desirable in order to carry out known reactions under relatively mild conditions, to improve yields, and to increase the reactivity of less reactive substrates. For example, in the direct synthesis of Grignard reagents (organomagnesium reagents) from the reaction of magnesium metal and an organic halide, higher reaction temperatures and more strongly coordinating solvents have been used to improve yields. Also, methods have been developed to activate the magnesium metal using iodine or catalytic amounts of ethylene bromide or ethyl bromide. In the synthesis of organozinc compounds from the oxidative addition of zinc metal to alkyl iodides, several methods have been used to activate zinc towards oxidative addition reactions. These include washing the zinc metal with HCl solution, using a Zn—Cu couple, and metal-solvent cocondensation, for example. In spite of these methods, the direct oxidative addition of zinc metal to organic halides has been limited to relatively reactive halides such as alkyl iodides or α-haloesters. Most alkyl bromides, alkyl chlorides, vinyl halides, and aryl halides do not directly react with zinc metal.

Other approaches used to generate highly reactive zerovalent metals include-metal atom vapor techniques, ultrasound techniques, and the reduction of metal halide salts. The zerovalent metal species produced from the reduction of metal halide salts are typically more reactive and better synthetic tools than are commercial metals or metals produced from standard activating techniques. The properties of the zerovalent metals produced are, however, generally dependent upon the solvent used, the reducing agent, and the halide anion of the metal salt being reduced. For example, magnesium metal in the form of a black powder can be obtained by reducing magnesium halide salts in an ethereal solvent with molten sodium or potassium. However, the use of an alkali metal in conjunction with an electron carrier such as naphthalene can produce magnesium powder of different reactivity. Furthermore, $MgCl_2$ typically produces a more reactive zerovalent metal than does $MgF_2$.

There is a continuing need for highly reactive zerovalent metals that can be utilized in a broad spectrum of syntheses of various chemical compounds. An object of the invention is to produce zerovalent metal species that are more reactive, or possess different reactivity, than those obtained from traditional methods. Another object of the invention is to produce zerovalent metal species that are highly reactive towards oxidative addition. Yet another object of the invention is the direct production of a wide variety of organometallic compounds, e.g., aryl, heterocyclic, arylalkyl, and polymeric metal reagents that can undergo a number of valuable synthetic reactions. Still another object of the invention is to produce a wide variety of organometallic reagents that contain a broad spectrum of functional groups such as esters, ketones, nitriles, halides, amides, carbamates, epoxides, aldehydes, α,β-unsaturated enones (e.g., esters and ketones), sulfoxides, sulfones, etc.

SUMMARY OF THE INVENTION

These and other objects are achieved by the present invention which is directed to the preparation of highly reactive zerovalent metal species containing cyanide salt(s). Such metal species can be used to form new organometallic reagents, which can be used in a wide variety of synthetic reactions. As used herein, the phrase "highly reactive" refers to the reactivity of the metal species in organic reactions, particularly oxidative addition reactions. A zerovalent metal species is "highly reactive" if it reacts with a wide variety of primary, secondary, and tertiary alkyl, vinyl, and aryl halides in relatively high yields, for example, in greater than about 30% yields, preferably in greater than about 50% yields, and more preferably in greater than about 70% yields.

A highly reactive zerovalent metal species of the present invention is composed of formally zerovalent metal atoms in mixture or combination with a cyanide salt. Preferably, the formally zerovalent metal atoms are in mixture or combination with a cyanide salt and a halide salt. The cyanide salt, and halide salt if present, is preferably a salt in which the counterion is generated from the reducing agent used to produce the zerovalent metal species. More preferably, the counterion in the cyanide salt, and the halide salt if present, is an alkali metal or an alkaline earth metal. Most preferably, the counterion in these salts is an alkali metal.

The highly reactive metal species of the present invention are in a finely divided powdered form. By "finely divided" it is meant that the particles are typically of less than about 3 microns in diameter. Preferably, they are of about 1–2 microns, although they can be on the submicron level. The powders can be so finely divided that they form suspensions in a solvent and do not readily settle or filter out of the solvent. Typically, however, the zerovalent metal species of the present invention are not completely soluble in organic solvents. Furthermore, such species contain no direct metal-carbon bonds because they are prepared from the reduction of a metal cyanide salt containing no organic groups.

In the present invention, the highly reactive zerovalent metal species readily undergo oxidative addition to organic compounds under mild conditions to generate corresponding organometallic reagents in excellent yields. Preferably, the organic compounds are highly functionalized organic compounds. An organometallic reagent of the present invention includes a mixture or combination of an organic mono- or poly-metal compound and a salt of a cyanide. The organic radical of the metal compound is an aliphatic, aryl, heterocyclic, arylalkyl, or polymeric group. Preferably, the organic radical of the metal compound is an aliphatic, aryl, heterocyclic, or arylalkyl group. Also, preferably, the organometallic reagent of the present invention includes a mixture or combination of an organic mono- or poly-metal compound and an alkali metal salt of a cyanide.

In the context of the present invention, the term "aliphatic" means a saturated or unsaturated linear, branched, or cyclic hydrocarbon radical. This term is used to encompass alkyl and vinyl radicals, for example. The term "alkyl" means a saturated linear, branched, or cyclic hydrocarbon radical. The term "heterocyclic" means a mono- or polynuclear cyclic radical containing carbons and one or more heteroatoms such as nitrogen, oxygen, phosphorus, silicon, or sulfur or a combination thereof in the ring or rings. Such heterocycles include, but are not limited to, pyridine, pyrrol, indole, thiazole, pyrazine, guanine, cytosine, thyamine, adenine, uredine, uracil, oxazole, pyrazole, hydantoin, piperazine, quinoline, xanthene, 1,10-phenanthroline, thiophene, and acridine. The term "aryl" means a mono- or polynuclear aromatic hydrocarbon radical. The term "arylalkyl" means a linear, branched, or cyclic alkyl hydrocarbon radical having a mono- or polynuclear aromatic hydrocarbon or heterocyclic substituent. The term "polymeric" or "polymer" is used herein in its most general sense to mean a compound of repeating structural units.

The present invention is also directed to the preparation of an organometallic reagent. This method of preparation involves contacting an organic compound having one or more stable anionic leaving groups with a first combination of zerovalent metal atoms and a cyanide salt to produce a second combination of an organic mono- or poly-metal compound and the cyanide salt. Preferably the cyanide salt is a salt of an alkali metal. The organic radical of the organic compound having one or more stable anionic leaving groups is an aliphatic, aryl, heterocyclic, arylalkyl, or polymeric group.

DETAILED DESCRIPTION OF THE INVENTION

The present invention is based upon the discovery that highly reactive zerovalent metal species containing cyanide salts display surprising and unexpected reactivity and usefulness in organic synthetic procedures. For example, the highly reactive zerovalent metal species of the present invention display reactivity toward a wide variety of aliphatic, aryl, heterocyclic, arylalkyl, and polymeric organic compounds to form organometallic reagents. These organometallic reagents generally possess unique chemical reactivity and are typically stable and easy to manipulate. Of special note in preferred reactions of the zerovalent metal species with organic compounds is the toleration of a wide variety of functional groups, and often particularly unexpected functional groups. As a result, highly functionalized organometallic reagents can be prepared by preferred zerovalent metals of the present invention. This allows the synthesis of many molecules to be shortened considerably and made viable commercial candidates.

Specifically, the highly reactive zerovalent metals of the present invention will undergo oxidative addition to a wide variety of organic compounds, e.g., alkyl, vinyl, and aryl iodides, bromides, and chlorides, to generate the corresponding organometallic reagents. Significantly, most of these reactions can be carried out at room temperature or slightly above. The highly reactive zerovalent metals can also be used to carry out other name reactions on substrates that now are not possible using the standard forms of metals. Also, a number of intramolecular reactions can now be carried out.

The highly reactive metal species of the present invention is composed of formally zerovalent metal atoms. The formally zerovalent metal atoms are in combination with a cyanide salt, preferably a cyanide salt (or salts) and a halide salt (or salts). By "formally zerovalent" it is meant that the formal oxidation state, or charge, is equal to the group number of the metal minus the number of unshared electrons of the metal minus the number of bonds.

Preferably, the salts incorporated in the zerovalent highly reactive metal species are salts of an alkali metal or an alkaline earth metal. More preferably, they are salts of an alkali metal, i.e., Li, Na, K, Rb, or Cs. Most preferably, they are salts of Li. The counterions of the cyanide and halide salts typically are produced from the reducing agent, although they may also result from a coordinate complexing agent, such as an alkali metal halide, if present in the metal cyanide salt starting material.

The mixture or combination is in the form of a finely divided metal powder, which is generally highly dispersible in ethereal, polyethereal, or hydrocarbon solvents. The mixture or combination may be so finely divided, however, that the powders form suspensions in a solvent. The powders in such suspensions may not easily settle out of the solvent or be readily filtered out of the solvent. Typically, the zerovalent metal species of the present invention are not completely soluble in organic solvents, however.

Although not intending to be a limitation of the invention, it is believed that the highly reactive zerovalent metal species of the present invention are clusters of metal atoms. These metal atoms are believed to be associated in some manner with the cyanide salt, which is produced from the reducing agent and the cyanide anion of the metal salt starting material. If the metal salt starting material includes a halide-containing coordinate complexing agent, the metal atoms may also be associated in some manner with a halide salt or salts in addition to the cyanide salt or salts. The cluster-salt association is most likely a surface phenomenon and is believed to facilitate the oxidative transfer reaction between the zerovalent metal species and the organic compounds in the formation of the organometallic reagents. The zerovalent metal species of the present invention contain no direct metal-carbon bonds as they are prepared from the reduction of a metal cyanide salt containing no organic groups.

The zerovalent highly reactive metal species of the present invention is prepared from the reduction of any nonalkali metal cyanide salt, i.e., any metal which is not an alkali metal and which will form a cyanide salt. Although it is preferred that the metal cyanide salt be an isolatable and stable compound, this is not believed to be a necessity. That is, the metal cyanide salt could be formed in situ, as for example when a mixture of $MgCl_2$ and NaCN are reduced.

The zerovalent metal species of the present invention can include any zerovalent "nonalkali metal" of the Periodic Table. That is, the zerovalent metal species of the present invention can include any element having the metallic characteristics of low ionization energies, high electrical and thermal conductivity, ductility, malleability, and luster. This includes transition metals, i.e., those elements in the Periodic Table with their outermost electrons in "d" orbitals; lanthanides and actinides, i.e., those elements in the Periodic Table with their outermost electrons in "f" orbitals; the heavier elements of Group IIIA, i.e., Group 13 (Al, Ga, In, Tl); the heavier elements of Group IVA, i.e., Group 14 (Sn, Pb); the heavier elements of Group VA, i.e., Group 15 (Bi); and all the elements of Group IIA, i.e. Group 2, the alkaline earth metals. This does not include, however, the elements of Group IA, i.e. Group 1, the alkali metals, as indicated by the term "nonalkali metal" used herein. Alkali metals are not included within the scope of the present invention generally because they have too high a reduction potential. Furthermore, herein the metalloids (B, Si, Ge, As, Sb, Te) are not included within the meaning of the term "metal."

Preferably, the zerovalent metal species of the present invention are the stable, relatively long-lived isotopes of the metals listed above. More preferably, the zerovalent metal species of the present invention are selected from the group consisting of zerovalent Zn, Cu, Al, Mg, Ni, Fe, Cr, W, Pt, Pd, Ag, Au, U, Mn, V, Sn, Pb, In, Co, Cd, Tl, Ti, Sm, and Mo. Most preferably, they are selected from the group consisting of zerovalent Zn, Cu, Al, Mg, Ni, Fe, Cr, Pt, Pd, U, Co, Cd, and Ti.

Useful species that can be reduced to form the highly reactive zerovalent metal species of the present invention include, but are not limited to, $Zn(CN)_2$, $Zn(CN)_2 \cdot 2LiBr$, CuCN, $Cu(CN)_2$, $Cu(CN)_2 \cdot 2LiBr$, $Mg(CN)_2$, $Ca(CN)_2$, $Ba(CN)_2$, $Sr(CN)_2$, AgCN, $Cd(CN)_2$, $Co(CN)_2$, AuCN, $Au(CN)_3$, $In(CN)_3$, $Pb(CN)_2$, $Hg(CN)_2$, $Ni(CN)_2$, $Pd(CN)_2$, $Pt(CN)_2$, RbCN, TlCN, $U(CN)_4$, and $Ti(CN)_4$. Certain metal cyanide salts are hydrated, i.e., contain coordinated water molecules. Such salts are useable if the water molecules are driven off prior to use. This can be accomplished through the use of a vacuum techniques, for example. Thus, the useable metal cyanide salts of the present invention are anhydrous, i.e., substantially free of coordinated water molecules.

Many of the metal cyanide salts useable in the preparation of the zerovalent highly reactive metal species of the present invention can be obtained from commercial sources. For example, CuCN, AuCN, AgCN, $Zn(CN)_2$, and $Hg(CN)_2$ are available from Aldrich Chemical Company, Milwaukee, Wisc. Other cyanide salts can be prepared and isolated using known synthetic procedures. Still other cyanide salts can be prepared in situ, i.e., in the same reaction vessel in which the reduction occurs or prior to reduction without isolation of the cyanide salt. It is also within the scope of the present invention to reduce a mixture of a metal halide salt, such as $MgCl_2$, and an alkali metal cyanide, such as NaCN, to produce the resultant highly reactive metal species of the present invention. Such highly reactive metal species would contain zerovalent metal atoms in mixture or combination with a cyanide salt and a halide salt.

In addition to metal cyanide salts, which are generally insoluble in most ethereal, polyethereal, and hydrocarbon solvents, soluble forms of metal cyanide salts can be used in the method of the present invention. Such soluble forms generally include a halide-containing coordinate complexing agent. That is, a metal cyanide salt can be converted to a soluble form by coordinating it with a halide-containing coordinate complexing agent. Preferably, the coordinate complexing agent is an alkali metal halide salt, more preferably it is a lithium halide salt, and most preferably it is lithium bromide or chloride. Other solubilizing agents can also be used to assist in solubilizing the starting metal cyanide salt. One such agent is N,N,N',N'-tetramethylethylenediamine (TMEDA).

Generally, the reducing agent can be any reducing agent that is capable of reducing the metal cyanide salt of choice. To meet this condition, the reducing agent generally has a reduction potential at least about 100 mV more negative than that of the metal in the metal cyanide salt. It is noted that this differential of about 100 mV is independent of the reference electrode. In the reduction of a Zn(II) cyanide salt, a reducing agent having a reduction potential at least about 100 mV more negative than that of Zn(II) means that the reducing agent has a reduction potential of about −1.0 volts or more negative relative to the standard calomel electrode (SCE). In the reduction of a Cu(I) or Cu(II) cyanide salt, this typically means that the reducing agent has a reduction potential of about +0.90 volts relative to the standard calomel electrode (SCE).

Examples of useable reducing agents include, but are not limited to: alkali and alkaline earth metals; alkali and alkaline earth metal salts of aromatic anions (i.e., aromatic electron transfer compounds), such as sodium naphthalenide or lithium naphthalenide; metal hydrides, such as sodium borohydride or sodium hydride; metal intercalated graphites; and alkali metals dissolved in glymes or ethers. Preferably the reducing agent is an alkali metal reducing agent, such as an alkali metal, an alkali metal dissolved in glymes or ethers, or an alkali metal salt of an electron transfer compound. More preferably, the reducing agent is an alkali metal salt of an electron transfer compound, i.e., a combination of an alkali metal cation and an anion of an electron transfer compound, referred to herein as an "alkali metal complex." The electron transfer compound preferably has a reduction potential of −0.5 volts, versus the standard calomel electrode (SCE), or more negative. More preferably, the electron transfer compound is an aromatic electron transfer compound.

Examples of useful "alkali metal complex" reducing agents include, but are not limited to, complexes of an alkali metal and an aromatic electron transfer compound; alkali metal-polyether solvates; alkali metal-crown ether solvates; alkali metal-cryptate solvates, etc. Preferably, the alkali metal complex reducing agent is sodium naphthalenide, sodium anthracenide, sodium biphenylide, sodium benzophenone, potassium naphthalenide, potassium anthracenide, potassium biphenylide, potassium benzophenone, lithium naphthalenide, lithium anthracenide, lithium biphenylide, lithium benzophenone, cesium naphthalenide, cesium anthracenide, cesium biphenylide, or cesium benzophenone. More preferably, the reducing agent is a complex of an alkali metal cation and naphthalene. Most preferably, the reducing agent is a complex of lithium and naphthalene.

The alkali metal complex reducing agents, e.g., lithium naphthalenide, can also be generated by electrochemical reduction. This involves the electrochemical reduction of an electron transfer compound, e.g., naphthalene, using an alkali metal salt, e.g., a lithium halide, as the electrolyte. That is, an alkali metal complex reducing agent can be formed electrochemically. This can be carried out in an electrochemical cell containing an ethereal or polyethereal solvent using an electrode of palladium, platinum, carbon, or gold. Useful electrodes can be in any of a variety of forms. They can be solid, porous, or in the form of a slurry. The electrochemical route is advantageous and preferred at least because it avoids the use of alkali metals, which can be quite dangerous.

As a representative example of this procedure, naphthalene can be reduced in an inert atmosphere in the presence of a lithium salt, as the electrolyte, in THF. The electrode can be a large surface area electrode to facilitate the reduction. Once the lithium naphthalenide is formed, it can be transferred to the metal cyanide salt, or the metal cyanide salt can be transferred to it, for formation of the zerovalent highly reactive metal species.

The process of reduction of the various metal cyanide salts to produce the zerovalent highly reactive metal species of the present invention is conducted under conditions designed to prevent its reoxidation. Generally, these conditions include use of a nonhydroxylic solvent, and the exclusion of oxygen. Also, the conditions are controlled so as to promote the existence of the metal atoms as small clusters, preferably in the form of a finely divided powder, and to avoid their agglomeration into larger configurations.

Preferably, these conditions include temperatures of about 100° C. or less, an inert atmosphere, e.g., an argon or nitrogen atmosphere, and a reaction time of about ten hours or less. More preferably, the temperature is about 80° C. or less and the reaction time is about five hours or less. For the preparation of most zerovalent metals, such as Zn, Mg, Ni, Al, Mn, and Fe, the reactions are most preferably conducted at temperatures of about 20° C. to about 30° C., and the reaction time is about two hours or less. For the preparation of certain zerovalent metals, such as Cu, Ag, Au, U, and Ti, the reactions are most preferably conducted at temperatures of less that about −30° C., typically within a range of about −30° C. to about −100° C., and the reaction time is about one hour or less.

As stated above, the solvent is a nonhydroxylic solvent. Preferably, it is an ethereal, polyethereal, or hydrocarbon solvent. Examples of such solvents include ethyl ether, methyl-t-butyl ether, tetrahydrofuran (THF), 1,2-dimethoxyethane (DME or glyme), diglyme, triglyme, benzene, xylene, hexanes, and the like. More preferably, the reaction is carried out in an ethereal or polyethereal solvent, and most preferably in tetrahydrofuran. If a hydrocarbon solvent (e.g., benzene, xylene, hexanes, etc.) is used, it preferably contains a secondary solubilizing agent such as N,N,N',N'-tetramethylethylenediamine (TMEDA) to assist in solubilizing the starting materials. If the reducing agent is an alkali metal reducing agent, but not an alkali metal salt of an electron transfer compound, the solvent is one whose boiling point exceeds the melting point of the alkali metal.

There are certain practical considerations that should be taken into account when choosing THF or DME as the solvent of choice. For instance, DME is preferred when higher reaction temperatures are desired. However, the formation of lithium naphthalenide is much more facile in THF than in DME. Furthermore, the solubility of the metal cyanide salt may be a consideration in the choice of solvent. Solubility of the metal cyanide salt allows for more convenient transfer of the metal cyanide when necessary.

There are several methods of preparation of the zerovalent highly reactive metal species of the present invention. For example, the zerovalent metal species can be prepared by the combination of an equivalent amount of an alkali metal, such as K or Na, in a solvent whose boiling point exceeds the melting point of the alkali metal, such as THF or glyme. This method is represented by the reduction of $Zn(CN)_2$ in Example 1.

Herein, by "an equivalent amount" or a reducing agent, it is meant that about one mole, i.e., about 0.8–1.2 moles, of an alkali metal is used per mole of metal cyanide salt when the metal is in the +1 oxidation state (MCN). Alternatively, about two moles, i.e., about 1.8–2.2 moles, of an alkali metal are used per mole of metal cyanide salt when the metal is in the +2 oxidation state ($M(CN)_2$). Similarly, about three moles, i.e., about 2.8–3.2 moles, of an alkali metal are used per mole of metal cyanide salt when the metal is in the +3 oxidation state ($M(CN)_3$). Furthermore, about four moles, i.e., about 3.8–4.2 moles, of an alkali metal are used per mole of metal cyanide salt when the metal is in the +4 oxidation state ($M(CN)_4$).

Another method for the preparation of a reactive metal species involves a one-step reduction of a metal cyanide salt. This method is represented by the reduction of $Zn(CN)_2$ in Example 2. Specifically, this method includes the reduction of a metal cyanide salt in the presence of an alkali metal, such as lithium, and an effective catalytic amount of an electron transfer compound, such as the aromatic electron transfer compound naphthalene. With respect to this method, by an "effective catalytic amount" it is meant that a sufficient amount of the electron transfer compound is present to effect the reduction in less than about 24 hours, preferably in less than about 10 hours. The electron transfer compound is typically present in no greater than about 10 mole %, preferably no greater than about 6 mole %, and most preferably within a range of about 2 mole % and about 5 mole %, of the alkali metal present. The alkali metal is present in an equivalent amount, i.e., in a range of about 1.8–2.2 moles per mole of metal salt being reduced if the metal is in the +2 oxidation state, as with $Zn(CN)_2$. It is desirable, however, to use a slight excess of the metal salt relative to the alkali metal, to decrease the chance that the reducing agent could interfere with the subsequent use of the highly reactive metal.

The reduction is typically complete in about ten hours, and preferably in about five hours, with vigorous stirring of the mixture. For certain embodiments, the reaction is observed to be "complete" when the green color, which is evidence of an alkali metal/aromatic electron transfer complex, disappears. This occurs, for example, with the relatively insoluble $Zn(CN)_2$. For other embodiments, the reaction is observed to be "complete" when the green color appears, and remains. For example, this would occur if a soluble metal salt were used with an excess of the alkali metal and electron carrier, relative to the metal salt. For still other embodiments, completion of the reduction reaction is evidenced by the disappearance of lithium and/or lack of formation of the bright green lithium naphthalenide anion.

In this one-step preparation method with soluble metal cyanide salts, the solubilized salt is generally always in excess in the reaction flask, relative to the amount of the alkali metal/electron transfer complex present. Herein, "solubilized" salt means the portion of the metal cyanide salt that has gone into solution. With generally insoluble metal cyanide salts, such as $Zn(CN)_2$ in THF, the formation of the alkali metal/electron transfer complex is faster than the dissolution of the metal salt. Thus, the alkali metal complex is generally always in excess in the reaction flask, relative to the amount of the solubilized salt. Although this has been observed for these particular species, this is not meant to be a limitation of the invention.

For soluble metal cyanide salts, this one-step method of Example 2 is not necessarily the most preferred method of reduction because the surface of the lithium metal can be coated with the zerovalent highly reactive metal, which slows down the reduction. For the insoluble metal salts, however, this is the most preferred method of reduction because it yields a very reactive metal using a simple one-step procedure.

A third method for the preparation of a reactive metal species involves a two-step reduction of a metal cyanide salt using a preformed reducing agent. This method is represented by the reduction of $Zn(CN)_2$ in Example 3 and CuCN.2LiX in Example 4. By "preformed" it is meant that for each mole of the alkali metal, about 1.0–1.2 moles of an electron transfer compound are allowed to react substantially completely, i.e., until substantially all the alkali metal is consumed, before contacting the metal cyanide salt. The formation of the preformed reducing agent preferably takes place in an ethereal, polyetheral, or hydrocarbon solvent, and generally is substantially complete in less than about eight hours, preferably in less than about three hours.

An approximate equivalent amount of the metal cyanide salt in a solvent is then slowly (over a period of about 5–15 minutes) transferred into the solution of the preformed reducing agent, e.g., lithium naphthalenide in THF. Alternatively, the preformed reducing agent can be added to the metal salt. Preferably, the procedure is carried out in this latter way if the metal cyanide salt is relatively insoluble in the solvent chosen. Whichever the direction of transfer, it is preferably done at a rate to ensure that the preformed reducing agent is in excess relative to the solubilized metal. For the more soluble metal salts, the transfer of the preformed reducing agent to the metal salt is done more slowly (over a period of about 15–120 minutes) than the transfer of the preformed reducing agent to the metal salt. In this way, the reactivity of the resultant zerovalent metal powder is not decreased, which is believed to result from unreduced metal ions being adsorbed on the metal surface.

The reduction of the metal cyanide salt in the second step of this two step method using a preformed reducing agent is typically carried out in less than about eight hours, preferably in less than about two hours, and more preferably in less than about one hour. Preferably, the total reaction time for both steps is less than about eight hours. This two-step method is advantageous for soluble metal cyanide salts at least because it involves a shorter reaction time and it decreases, if not eliminates, the problem of the resultant reduced metal coating the alkali metal.

A fourth method for the preparation of a reactive metal species involves a two-step reduction of a metal cyanide salt in the presence of an excess of an alkali metal. This method is represented by the reduction of $Zn(CN)_2 \cdot 2LiBr$ in Example 5. The reducing agent is formed from an alkali metal and an effective catalytic amount of an electron transfer compound. By an "effective catalytic amount" it is meant that a sufficient amount of the electron transfer compound is present to effect the reduction in less than about three hours, preferably in less than about two hours. Preferably, this involves the use of no greater than about 10 mole % of the electron transfer reagent, more preferably no greater than about 6 mole %, and most preferably within a range about 2 to about 5 mole %, of the alkali metal present. The alkali metal is present in an equivalent amount of metal cyanide salt being reduced, e.g., within a range of about 1.8–2.2 moles per mole of MCN salt being reduced or 2.8–3.2 moles per mole of $M(CN)_2$ salt being reduced. Thus, a solution of the resultant alkali metal complex reducing agent, i.e., the complex of the alkali metal and electron transfer compound, contains unreacted alkali metal.

A metal cyanide salt, preferably a metal salt solution, e.g., $Zn(CN)_2 \cdot 2LiBr$ in THF, or a metal salt suspension, e.g., $Zn(CN)_2$ in THF, is then slowly transferred into the solution of the alkali metal reducing agent, e.g., lithium naphthalenide in THF, containing unreacted alkali metal, e.g., lithium. By "slowly" it is meant that the metal cyanide salt is added to the solution of the reducing agent containing unreacted alkali metal at a rate that ensures the presence of excess alkali metal complex reducing agent relative to solubilized metal salt. This is evidenced by adding the metal salt at a rate such that the color of the reducing agent solution remains dark green, if a complex of an alkali metal and aromatic electron transfer compound is used. Although not intending to be a limitation to the invention in any way, it is believed that as the reducing agent is consumed, the recovered naphthalene reacts with the unreacted lithium to form lithium naphthalenide until all the lithium is consumed. This is unexpected because the small amount of electron carrier is expected to lead to long reduction times of several hours and even days, rather than minutes. In contrast, the relatively short reduction times with a small amount of electron carrier makes this an especially appealing method.

This latter method is the most preferred of the methods specifically described, especially for the relatively soluble metal cyanide salts, at least because a more reactive and uniform zerovalent metal species is produced. Furthermore this method can greatly shorten the reduction time. For example, the highly reactive metal species can be formed in less than about three hours, preferably in less than about two hours, more preferably in less than about one hour, and most preferably in less than about 30 minutes, from the time the soluble metal cyanide salt is initially added to the alkali metal complex reducing agent. Also, as compared to the method using a preformed reducing agent, this method reduces the amount of electron transfer agent required. Thus, this method is especially useful for large scale reactions. In some situations, however, such as when a relatively insoluble metal cyanide salt like $Zn(CN)_2$, is used, the method of Example 2 may be preferred, even if the reaction times are longer, at least because everything can be carried out in a single flask, i.e., no transfers are necessary, and the amount of electron transfer compound required is small.

The physical appearance of the zerovalent highly reactive metal formed from any of the methods described herein typically depends on the rate of stirring and/or the rate of transfer. For example, a slow addition of about three seconds per drop generally results in an extremely fine black slurry of active metal. Such a slurry typically takes several hours to settle and can easily be transferred by a cannula. With faster addition, about one second or less per drop, the active metal formed can be sponge shaped. Although it is believed that either of these physical forms of the metal does not detrimentally effect its reactivity, if the metal is not in a finely divided form, i.e., if it is sintered into large shiny pieces, it will not be very reactive.

Whichever method is chosen, the zerovalent highly reactive metal species is typically in the form of a finely divided black powder. Once formed it can usually be isolated and washed to remove any unreacted starting materials, side products, or excess reducing agent, if so desired. This is typically done in situations in which naphthalene is perceived as presenting a problem with product isolation or if a different solvent is desired. The highly reactive zerovalent metal species may be used in the medium in which it was prepared, however, particularly if the particles are very small and a suspension is formed.

Most of the zerovalent highly reactive metal species of the present invention can be isolated, are stable, and can be stored for several years at temperatures ranging from 0° C. to 30° C. They can be stored in a dry state, in mineral oil as a paste, in an ethereal or hydrocarbon solvent as a suspension, or in a paraffin wax matrix. It is desirable, however, for the zerovalent highly reactive metal species to be stored under an inert atmosphere of argon or nitrogen. In some instances, however, certain zerovalent metal species are preferably synthesized immediately before use, especially for those that are extremely reactive.

The zerovalent highly reactive metal species of the present invention readily undergo a variety of reactions with organic compounds. For example, the highly reactive zinc, produced from the reduction of $Zn(CN)_2$, undergoes oxidative addition to a wide variety of organic compounds to form organozinc reagents. Representative reactions are presented in Example 7. Significantly, the reaction will tolerate a wide spectrum of functional groups on the organic compounds. These organozinc reagents can be used to create unique organic species, such as highly functionalized biphenyl compounds, highly functionalized benzene derivatives, symmetrical and unsymmetrical substituted 1,3-butadienes, highly functionalized ketones, esters, amides, nitriles, or halides, or known organic compounds from unique synthetic routes.

Representative reactions of the zerovalent copper species, produced from the reduction of $CuCN \cdot 2LiBr$, are presented in Example 8. Significantly, the zerovalent copper species reacts with alkyl, allylic, vinyl or phenyl halides and acetates at low temperature, such as $-100°$ C., preferably $-70°$ C., to produce the corresponding alkyl, allylic, vinyl, pyridyl, 2-methylenylpyridyl or phenyl organocopper reagent with less than 10% of the homocoupled by-product.

Generally, the organometallic reagent of the present invention includes an aliphatic, aryl, heterocyclic, arylalkyl, or polymeric mono- or poly-metal compound in mixture or combination with a cyanide salt. Preferably, the organometallic reagent is a mixture or combination of an aliphatic, aryl, heterocyclic, arylalkyl, or polymeric mono- or poly-metal compound, a cyanide salt, and a halide salt. The cyanide and halide salts preferably include alkali metal counterions or alkaline earth metal counterions, and more preferably the salts include alkali metal counterions. The metal moiety, cyanide salts, and halide salts if present, are generally derived from the foregoing zerovalent metal species. Although not intending to be a limitation of the invention, it is believed that the metal moiety or moieties of the organic metal compound associate in some manner with the cyanide salt present, and any other salts present, to form the organometallic reagent. It is further believed that this association is in part responsible for the novel and selective reactivity of the organometallic reagents of this invention.

The molecular size of the organometallic reagents can range from monomeric organic compounds, typically having from 1 to about 300 carbons, to polymeric compounds having molecular weights up to and including the million range. The organic radical of the organometallic compounds can be an aliphatic, aryl, arylalkyl, heterocyclic, or polymeric group. That is, the organic radical can be saturated, unsaturated, cyclic, aromatic, or heterocyclic containing nitrogen, oxygen, sulfur, phosphorus, silicon, or combinations thereof in the heteronucleus. Preferably, the organic radical of the organometallic compounds is an aliphatic, aryl, heterocyclic, or arylalkyl group, and more preferably an arylalkyl or heterocyclic group.

Preferred aliphatic, aryl, heterocyclic, and arylalkyl groups include linear or branched alkyl, cycloalkyl, allyl, vinyl, phenyl, benzyl, pyridyl, quinolinyl, piperadinyl, cytosinyl, uracinyl, quaninyl, adenosinyl, pyrrolyl, thiazolyl, thiophene, and phenyl alkyl groups, as well as the hydrocarbon substituted and/or functionalized forms thereof. The hydrocarbon substituents can be one or more of such groups as alkyl, cycloalkyl, heterocyclic, olefinic, and aromatic groups as well as combinations thereof, each substituent preferably having from 1 to about 30 carbon atoms.

The aliphatic, aryl, arylalkyl, heterocyclic, or polymeric group of the organometallic reagents may optionally, and preferably, be functionalized with such groups as amides, nitriles, esters, ketones, allyls, ethers, carbamates, acetyls, imines, enones, epoxides, olefins, aldehydes, sulfoxides, sulfones, other halides, or any combination of these groups. More preferably, these functional groups are esters, nitriles, ketones, amides, halides, acetyls, enones, epoxides, olefins, ethers, or any combination of these groups.

The organometallic reagents are produced by the reaction of the highly reactive metal species of the present invention with an organic compound having at least one stable anionic leaving group. That is, the method for preparation of an organometallic reagent of the present invention includes contacting an organic compound having one or more stable anionic leaving groups with a first combination of zerovalent metal atoms and a cyanide salt to produce a second combination of an organic mono- or poly-metal compound and the cyanide salt.

The organic compound having at least one stable anionic leaving group, i.e., the starting material, preferably includes an organic radical selected from an aliphatic, aryl, heterocyclic, arylalkyl, and polymeric radical, more preferably, an aliphatic, aryl, heterocyclic, and arylalkyl group, and most preferably, a heterocyclic group, such as sulfur, oxygen, nitrogen, etc., as discussed above. The organic radical can optionally, and preferably, be functionalized with amides, nitriles, esters, ketones, allyls, ethers, carbamates, acetyls, imines, enones, epoxides, olefins, aldehydes, sulfoxides, sulfones, other halides, or any combination of these groups. More preferably, these functional groups are esters, nitriles, ketones, amides, halides, acetyls, enones, epoxides, olefins, ethers, or any combination of these groups.

The stable anionic leaving group of the organic compound starting material can be a halide, tosylate, phosphate, phosphite, triflate, phenolate, brosylate, trialkyl amine, triaryl amine, mixed tri(alkyl/aryl)amine, trialkyl phosphine, triaryl phosphine, mixed tri(alkyl/aryl)phosphine, trialkyl stannane, triaryl stannane, mixed tri(alkyl/aryl)stannane, thiophene ($-SC_6H_5$), phenolate ($-OC_6H_5$), and the like. By "mixed tri(alkyl/aryl)" amine, phosphine, stannane, it is meant that the nitrogen, phosphorus, and tin can be substituted with both alkyl and aryl groups. For example, the anionic leaving group can be $P(CH_3)_2(C_6H_5)$. Preferably, the anionic leaving group is a halide or triflate, and more preferably, a halide. Most preferably, the halide groups are iodide, chloride, and bromide.

The reactions between the zerovalent metal species and the organic compounds are generally conducted under conditions designed to preserve the integrity of the organometallic reagents. These conditions include, for example, the exclusion of water and oxygen. Typically, the reactions are carried out in the same medium used to produce the highly reactive metal species. Preferably, the reactions are carried out in an ethereal, polyethereal, or hydrocarbon solvent. More preferably, the reactions are carried out in an ethereal or polyethereal solvent. Most preferably the reactions are carried out in THF.

The reactions of organic compounds with a stable leaving group, e.g., organic halides, with the zerovalent highly reactive metal species of the present invention are typically carried out at a temperature of about $-110°$ C. to about $250°$ C., preferably at about $-30°$ C. to about $150°$ C. More preferably, the reactions are carried out at a temperature less than about $100°$ C. Most preferably, the reactions are carried out at a temperature of about $20°$ C. to about $100°$ C. The reactions are typically complete within about six hours, and preferably within about two hours.

The highly reactive metal species and the reactive organic compound, e.g., organic halide, with which it reacts, are preferably present in an amount such that the ratio of metal to reactive organic compound is about 0.9–4 moles of metal to 1 mole of reactive organic compound. More preferably, the ratio is 0.9–1.1 moles metal to 1 mole reactive compound, i.e., about an equimolar amount. Most preferably, the metal is present in an excess amount, i.e., at least about 1.1 moles metal to 1.0 mole reactive organic compound.

Although the organometallic reagents contain functional groups such as allyls, ethers, esters, nitriles, amides, ketones, etc., they are generally stable at ambient temperatures. That is, they do not typically self-react, or otherwise decompose, to a significant extent. To prevent any significant amount of decomposition, the organometallic reagents of the present invention are preferably stored within a temperature range of about −100° C. to about 200° C., under argon or nitrogen.

The following Examples are intended to illustrate the above invention and should not be construed as to narrow its scope. One skilled in the art will readily recognize that these Examples suggest many other ways in which the present invention could be practiced. It should be understood that many variations and modifications may be made while remaining within the scope of the invention.

EXPERIMENTAL EXAMPLES

Reactions were carried out on a dual manifold vacuum/argon system. The Linde™ prepurified grade argon was further purified by passing it through a 150° C. catalyst column (BASF R3–11) and then through a column of phosphorous pentoxide, followed by a column of granular potassium hydroxide. The handling of air-sensitive materials was performed, whenever possible, under argon in a Vacuum Atmospheres Company drybox. Chemical reagents were primarily purchased from commercial sources and were used as received. CuCN, NaCN, $MgCl_2$, and $Zn(CN)_2$ were purchased from Aldrich Chemical Co., Inc., Milwaukee, Wisc. $Zn(CN)_2$ was dried by heating at 250° C. under vacuum for 24 hours and stored in a drybox. THF and DME were freshly distilled before use from sodium/potassium alloy under a purified argon atmosphere. Low temperature conditions were maintained by utilizing a Neslab endocal ULT-80 refrigerated circulating bath or by utilizing dry ice/acetone baths.

EXAMPLE 1

Preparation of Highly Reactive Metals From Cyanide Salts Using an Alkali Metal and $Zn(CN)_2$ A predried 50 mL, two-necked, round-bottomed flask is equipped with a rubber septum, a condenser topped with an argon inlet, and a Teflon-coated magnetic stir bar. It is then charged with freshly cut lithium (21.90 mmol) and $Zn(CN)_2$ (11.49 mmol). Freshly distilled THF (20 mL) is added. The mixture is stirred at room temperature until all the lithium disappears, which evidences that the reduction is complete. The activated zinc appears as a fine black powder.

EXAMPLE 2

Preparation of Highly Reactive Metals From Cyanide Salts Using a One-Step Method and $Zn(CN)_2$ A predried 50 mL, two-necked, round-bottomed flask was equipped with a rubber septum, a condenser topped with an argon inlet, and a Teflon-coated magnetic stir bar. It was then charged with freshly cut lithium (0.152 g, 21.90 mmol), $Zn(CN)_2$ (1.35 g, 11.49 mmol), and naphthalene (0.144 g, 1.25 mmol). Freshly distilled THF (20 mL) was added. The mixture was stirred at room temperature until the green color disappeared, which evidenced that the reduction was complete (about 5 hours). The activated zinc appeared as a fine black powder. The formation of lithium naphthalenide by this method is faster than the rate of $Zn(CN)_2$ dissolution. Therefore, as little as 2–5 mole % of naphthalene can be used as an electron carrier.

EXAMPLE 3

Preparation of Highly Reactive Metals From Cyanide Salts Using a Two-Step Method, Preformed LiNp, and $Zn(CN)_2$ Two 50-mL two-necked flasks A, and B, were equipped with stir bars. Flask A was charged with freshly cut lithium (0.152 g, 21.9 mmol) and a slight excess of naphthalene (2.82 g, 22.0 mmol). Flask B was charged with anhydrous $Zn(CN)_2$ (1.35 g, 11.49 mmol). Both of these operations were performed in an argon atmosphere drybox. The flasks were then transferred to a manifold system and fitted with argon inlets. Freshly distilled THF (30 mL) was added to both flask A and B via a syringe. The mixtures were stirred at room temperature. The solution in flask A changed from colorless to dark green almost immediately. The lithium was consumed in about two hours forming the preformed lithium naphthalenide (LiNp). The preformed LiNp was then transferred dropwise to the $Zn(CN)_2$/THF dispersion via cannula over a period of 30 minutes.

EXAMPLE 4

Preparation of Highly Reactive Metals From Cyanide Salts Using a Two-Step Method, Preformed LiNp, and CuCN.2LiX Using CuCN.2LiBr Lithium (8.46 mmol) and naphthalene (10.1 mmol) were combined with anhydrous tetrahydrofuran (THF) (15 mL) and stirred under argon until the Li was consumed (approximately 2 hours). The flask was then cooled to −100° C. CuCN (8.00 mmol) and LiBr (17.27 mmol) in THF (5 mL) were stirred under argon until the Cu(I) salt was solubilized. The CuCN.2LiBr solution was cooled to −40° C. and transferred into the lithium naphthalide (LiNp) with a cannula. The solution was stirred for 5 minutes. The resulting zerovalent copper species, i.e., active copper, was ready for immediate use.

Using CuCN.2LiCl

Lithium (14.0 mmol) and naphthalene (15.1 mmol) were placed in a 100-mL round-bottomed flask in an argon dry box and sealed with a rubber septum. In the same argon dry box, CuCN (12.0 mmol) and LiCl (23.1 mmol) were placed in a 50-mL round-bottomed flask and sealed with a rubber septum. The two round-bottomed flasks were connected to a dual manifold vacuum-argon line. All steps were conducted under a positive pressure of argon. Dry THF (20 ml) was added to the flask containing the Li and naphthalene and the dark green solution was allowed to stir for 2½ hours. During this time, 12 mL of dry THF was added to the flask containing the CuCN and LiCl. The solution turned a pale yellow. The LiNp solution was then cooled to −100° C. (4:1 hexane/$Et_2O$ mixture in liquid $N_2$) and the CuCN.2LiCl was cooled to 0° C. The CuCN.2LiCl was transferred via cannula to the LiNp solution at −100° C. and stirred for 10 minutes. The resulting zerovalent copper species, i.e., active copper, was ready for immediate use.

EXAMPLE 5

Preparation of Highly Reactive Metals From Cyanide Salts Using a Catalytic Method and Soluble Metal Cyanide Salts Two 50-mL two-necked flasks, A and B, are equipped with rubber septa, condensers topped with argon inlets, and Teflon-coated magnetic stir bars. Flask A is charged with freshly cut lithium (30.63 mmol) and a catalytic amount of naphthalene (1.558 mmol). Flask B is charged with a soluble metal cyanide salt such as $Zn(CN)_2 \cdot 2LiBr$ (15.57 mmol). Both of these operations are performed in an argon atmosphere drybox. The flasks are then transferred to a manifold system and fitted with argon inlets. Freshly distilled THF (15 mL) is added to both flask A and B via a syringe. The mixtures are stirred at room temperature. The metal cyanide/ THF solution is transferred dropwise to flask A by a cannula at a rate that allows the color of the solution to remain a dark green.

EXAMPLE 6

Preparation of Highly Reactive Metals From Cyanide Salts Using a Halide Salt and an Alkali Metal Cyanide Two 50-mL two-necked flasks A, and B, are equipped with stir bars. Flask A is charged with freshly cut lithium (21.9 mmol) and a slight excess of naphthalene (22.0 mmol). Flask B is charged with anhydrous $MgCl_2$ (11.49 mmol) and anhydrous NaCN (23.0 mmol). Both of these operations are performed in an argon atmosphere drybox. The flasks are then transferred to a manifold system and fitted with argon inlets. Freshly distilled THF (30 mL) is added to each flask via a syringe. The mixtures are stirred at room temperature. Once the lithium is consumed, typically in about two hours, the preformed lithium naphthalenide (LiNp) is transferred dropwise to the mixture of $MgCl_2$ and NaCN via cannula.

EXAMPLE 7

Representative Reactions of Highly Reactive Zerovalent Zinc

Preweighed p-bromotoluene (0.92 g, 5.38 mmol) was added neat via a syringe to the highly reactive zinc, prepared as described in Example 2 (10.95 mmol). The reaction mixture was stirred at room temperature and monitored by GC. After 12 hours, the reaction was completed. The preparation of organozinc compounds from various organic halides and the highly reactive zinc prepared as described in Example 2 are summarized in Table I below.

TABLE I

Preparation of Organozinc Compounds Using Highly Reactive Zinc Prepared From $Zn(CN)_2$

| No. | Organic Halides | ZN:RX (Ratio) | Temp (°C.) | Time (hours) | Yield[a] (%) |
|---|---|---|---|---|---|
| 1 | p-BrC$_6$H$_4$CH$_3$ | 2:1 | 23° C. | 12 | 100 |
| 2 | p-BrC$_6$H$_4$CH$_3$ | 2:1 | 23° C. | 12 | 100 |
| 3 | p-BrC$_6$H$_4$CH$_3$ | 2:1 | Reflux | 12 | 100 |
| 4 | Cl(CH$_2$)$_3$CN | 2:1 | Reflux | 1 | 100 |

TABLE I-continued

Preparation of Organozinc Compounds Using Highly Reactive Zinc Prepared From $Zn(CN)_2$

| No. | Organic Halides | ZN:RX (Ratio) | Temp (°C.) | Time (hours) | Yield[a] (%) |
|---|---|---|---|---|---|
| 5 | Cl(CH$_2$)$_3$CO$_2$Et | 2:1 | Reflux | 1 | 100 |
| 6 | 5-BrC$_6$H$_4$-1,2,4-(CH$_3$)$_3$ | 2:1 | Reflux | 6 | 100 |

[a]The percent yield was determined by gas chromatography (GC) after hydrolysis with dilute HCl solution.

EXAMPLE 8

Representative Reactions of Highly Reactive Zerovalent Copper

Functionalized organocopper reagents were prepared from organic halides and the zerovalent copper species prepared according to the procedure of Example 4. These organocopper reagents can be cross-coupled with benzoyl chloride at −35° C. in 30 minutes to produce functionalized ketones in good to excellent yields (Table II).

A representative procedure for the formation of a functionalized ketone is as follows. The active copper species from Example 4 in THF was warmed to −35° C. and charged with ethyl 4-bromobutyrate (1.95 mmol). The solution was stirred for 10 minutes. (For aryl halides, the solution was warmed to 0° C., immediately charged with aryl halide, and allowed to mix for 1 hour.) The resultant organocopper reagent was ready for use in acid chloride coupling reactions or conjugate addition reactions. To the organocopper reagent was added benzoyl chloride (3 equivalents based on the amount of organocopper reagent used) neat via syringe at −35° C. The solution was stirred for 30 minutes, quenched with NH$_4$Cl (satd, 5 mL), and isolated with standard flash silica gel chromatographic techniques.

TABLE II

Cross-Coupling of Benzoyl Chloride with Organocopper Reagents Derived from CuCN.2LiBr-Based Copper

| entry | halide (equiv)[a] | product[b] | % yield[c] |
|---|---|---|---|
| 1 | Br(CH$_2$)$_7$CH$_3$(0.25) | PhCO(CH$_2$)$_7$CH | 82 |
| 2 | Br(CH$_2$)$_6$Cl(0.25) | PhCO(CH$_2$)$_6$Cl[3] | 80 |
| 3 | Br(CH$_2$)$_3$CO$_2$Et(0.25) | PhCO(CH$_2$)$_3$CO$_2$Et | 81 |
| 4 | Br(CH$_2$)$_2$CO$_2$Et(0.25) | PhCO(CH$_2$)$_2$CO$_2$Et | 43 |
| 5 | Br(CH$_2$)$_3$CN(0.25) | PhCO(CH$_2$)$_3$CN | 86 |
| 6 | bromobenzene(0.20) | PhCOPh | 87 |
| 7 | p-BrC$_6$H$_4$CN(0.20) | p-NCC$_6$H$_4$COPh | 60 |
| 8 | o-BrC$_6$H$_4$CN(0.20) | o-NCC$_6$H$_4$COPh | 74 |
| 9 | o-BrC$_6$H$_4$CO$_2$Et(0.20) | EtO$_2$CC$_6$H$_4$COPh | 51 |
| 10 | p-BrC$_6$H$_4$Cl(0.20) | P-ClC$_6$H$_4$COPh | 83 |

[a]Based on 1 equiv of CuCN, alkyl halides were allowed to react for 10 min at −35° C. Aryl halides were added at 0° C. and allowed to react for 1 h.
[b]All products gave consistent $^1$H and $^{13}$C NMR spectra.
[c]Isolated yields.

The foregoing discussion and examples are illustrative of the invention. However, since many embodiments of the invention can be made without departing from the spirit and scope of the invention, the invention resides wholly in the claims hereinafter appended.

What is claimed is:

1. A finely divided zerovalent metal species comprising a combination of formally zerovalent metal atoms selected from the group consisting of Zn, Al, Mg, Ni, Fe, Cr, W, Pt, Pd, Ag, Au, U, Mn, V, Sn, Pb, In, Co, Cd, Tl, Ti, Sm, and Mo and a cyanide salt.

2. The zerovalent metal species of claim 1 wherein the cyanide salt is an alkali metal salt of cyanide.

3. The zerovalent metal species of claim 1 further including a salt of a halide.

* * * * *